US010939864B2

(12) United States Patent
Barton et al.

(10) Patent No.: US 10,939,864 B2
(45) Date of Patent: Mar. 9, 2021

(54) FALLOPOSCOPE AND METHOD FOR OVARIAN CANCER DETECTION

(71) Applicants: Arizona Board of Regents on Behalf of the University of Arizona, Tucson, AZ (US); John Black, San Mateo, CA (US)

(72) Inventors: Jennifer Barton, Tucson, AZ (US); Urs Utzinger, Tucson, AZ (US); Tyler Tate, Tucson, AZ (US); Maureen Keenan, Tucson, AZ (US); John Black, San Mateo, CA (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 578 days.

(21) Appl. No.: 15/548,692

(22) PCT Filed: Feb. 3, 2016

(86) PCT No.: PCT/US2016/016456
§ 371 (c)(1),
(2) Date: Aug. 3, 2017

(87) PCT Pub. No.: WO2016/126879
PCT Pub. Date: Aug. 11, 2016

(65) Prior Publication Data
US 2018/0014773 A1  Jan. 18, 2018

Related U.S. Application Data

(60) Provisional application No. 62/111,440, filed on Feb. 3, 2015.

(51) Int. Cl.
*A61B 5/00* (2006.01)
*A61B 1/005* (2006.01)
(Continued)

(52) U.S. Cl.
CPC ........ *A61B 5/4325* (2013.01); *A61B 1/00009* (2013.01); *A61B 1/0051* (2013.01);
(Continued)

(58) Field of Classification Search
CPC ... A61B 5/6847; A61B 5/0071; A61B 5/4325; A61B 5/0035; A61B 5/7282;
(Continued)

(56) References Cited

U.S. PATENT DOCUMENTS 5,364,345 A  11/1994  Lowery et al.
5,807,239 A  9/1998  DiBernardo
(Continued)

FOREIGN PATENT DOCUMENTS

WO  WO 2013/029047  2/2013

OTHER PUBLICATIONS

J.F. Kerin, Chapter 10, Falloposcopy, Royal College of Obstetricians and Gynaecologists 1992, p. 169-184.*
(Continued)

*Primary Examiner* — Bo Joseph Peng
(74) *Attorney, Agent, or Firm* — Lathrop GPM LLP (57) ABSTRACT

A falloposcope is described, as is a method of screening a patient for fallopian tube and/or ovarian cancer with the Falloposcope. The falloposcope has an optical imaging subsystem capable of performing optical and fluorescence imaging, and an optical coherence tomography (OCT) channel, with a diameter of about 0.7 millimeter. The method includes inserting the falloposcope through a lumen of vagina, cervix, uterus, and fallopian tube such that a tip of the falloposcope is in proximity to a first fallopian tube or ovary of the patient; providing at least one fluorescence stimulus wavelength through an illumination fiber of the falloposcope, while imaging light at one or more fluorescence emission wavelengths through a coherent fiber bundle (Continued)

to form fluorescence emissions images; and determining suspect tissue from the fluorescence emission images. The OCT channel is also used to examine abnormalities in in-vivo female tissue, both to determine suspect tissue and analyze suspect abnormal tissue from fluorescence observations.

17 Claims, 9 Drawing Sheets (51) Int. Cl.
*A61B 1/00* (2006.01)
*A61B 1/04* (2006.01)
*A61B 1/06* (2006.01)
*A61B 1/07* (2006.01)
*A61B 1/303* (2006.01)

(52) U.S. Cl.
CPC .......... *A61B 1/0052* (2013.01); *A61B 1/0057* (2013.01); *A61B 1/00082* (2013.01); *A61B 1/043* (2013.01); *A61B 1/063* (2013.01); *A61B 1/0638* (2013.01); *A61B 1/0676* (2013.01); *A61B 1/0684* (2013.01); *A61B 1/07* (2013.01); *A61B 1/303* (2013.01); *A61B 5/0035* (2013.01); *A61B 5/0066* (2013.01); *A61B 5/0071* (2013.01); *A61B 5/0084* (2013.01); *A61B 5/6847* (2013.01); *A61B 5/6851* (2013.01); *A61B 5/7282* (2013.01); *A61B 5/0075* (2013.01)

(58) Field of Classification Search
CPC ... A61B 5/6851; A61B 5/0084; A61B 5/0066; A61B 5/0075; A61B 1/0051; A61B 1/07; A61B 1/0684; A61B 1/0676; A61B 1/0638; A61B 1/063; A61B 1/043; A61B 1/0057; A61B 1/0052; A61B 1/00082; A61B 1/00009; A61B 1/303
See application file for complete search history.

(56) References Cited

U.S. PATENT DOCUMENTS

| 2004/0245350 | A1 | 12/2004 | Zeng |
| 2004/0249243 | A1* | 12/2004 | Kleiner .............. A61B 1/00082 600/115 |
| 2005/0215911 | A1* | 9/2005 | Alfano ................... A61B 1/041 600/476 |
| 2012/0059220 | A1 | 5/2012 | Holsing et al. |
| 2012/0277528 | A1 | 11/2012 | Qiao |
| 2013/0226131 | A1 | 8/2013 | Bacino et al. |

OTHER PUBLICATIONS

International Search Report of PCT/US2016/016456 dated May 24, 2016, 3 pp.

* cited by examiner

Insert Hysteroscope through Vagina Into Uterus and Visualize Fallopian Tube Openings. 702

Apply visible light through illumination fiber. Use visible light images taken through the fiber-optic bundle of the falloposcope, and through the hysteroscope, and manipulation of steering wires of the falloposcope, to thread the falloposcope through the hysteroscope lumen, and into and through the fallopian tube to position the tip of the falloposcope at a viewing position adjacent an ovary 704

Perform visual inspection of fallopian tube interior during insertion of falloposcope through fallopian tube, to determine presence of suspect tissue in fallopian tube; inspect tissue closely if found. 706

At each viewing position, Illuminate with multiple wavelengths of fluorescent stimulus light, and image at fluorescent emissions wavelengths, to determine presence of suspect tissue. 708

Position optical coherence tomography channel adjacent to suspect tissue and perform optical coherence tomography to confirm or deny cancerous nature of the suspect tissue. 710

Repeat for second ovary, if present 712

FALLOPOSCOPE AND METHOD FOR OVARIAN CANCER DETECTION

CROSS-REFERENCE TO RELATED APPLICATIONS

The present application is a United States national phase entry of Patent Cooperation Treaty application number PCT/US2016/016456, which in turn claims priority to U.S. Provisional Patent Application Ser. No. 62/111,440 filed Feb. 3, 2015, the contents of both of which are incorporated herein by reference.

GOVERNMENT INTEREST

This invention was made with government support under Grant No. W81XWH-13-1-0131, awarded by ARMY/MRMC and Grant No. U54 EB015403, awarded by NIH. The government has certain rights in the invention.

BACKGROUND

Ovarian cancer is often detected at an advanced stage in part because symptoms are mild at early stages, and because there has been no readily available, low-cost, screening test. The risk of contracting ovarian cancer over a lifetime is about one in seventy, but is many times higher in high risk women such as those afflicted with the BRCA-1 or BRCA-2 genes. Seventy percent of women who develop this cancer die from it. Five-year survival for ovarian cancer following diagnosis at advanced stages could be increased from the current 50% to greater than 90% if the disease can be detected when still confined to the ovary.

Visual inspection of the ovaries in high risk women is possible with laparoscopy, but laparoscopy typically requires at least one incision through the abdominal wall with attendant pain, healing time, risk of infection, and anesthesia requirements; laparoscopic inspection of the ovaries is therefore uncommon. Further, some high-grade serous ovarian carcinomas have their origins in the fallopian tubular or endometrial epithelium, and may be missed by laparoscopic inspection.

Figure 1:
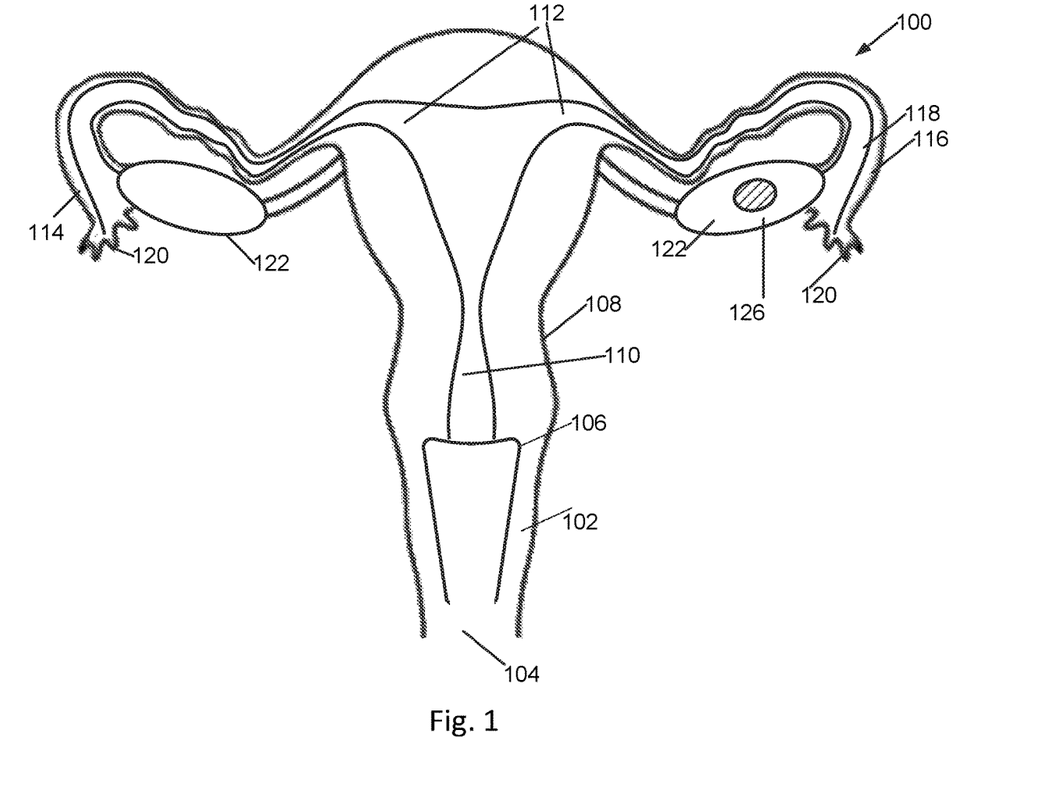
FIG. 1 is a sketch of the female reproductive system, showing lumens of the vagina, uterus, fallopian tube, and illustrating the ovaries.

The typical human female reproductive system 100 is illustrated in FIG. 1. A vagina 102 is a tubular structure that has an opening 104 outside the body and extends to the cervix 106 at the mouth of uterus 108. The uterus has a central passage or lumen 110 that communicates through the cervix 106 to a lumen of the vagina 102 and extends to and forks into a pair of fallopian tube mouths 112. The first 114 and second 116 fallopian tubes, each having a lumen 118, extend laterally from the uterus and terminate in ciliated fimbriae 120. The ciliated fimbriae are in close proximity to and partially surround a first 122 and second 124 ovary and serve to collect ova released by the ovary and direct them into the lumen on the associated fallopian tube. Depending on age and reproductive state of the patient, there may be one or more benign cysts or developing ova (not shown) on or near the ovarian surface. In some patients, there may be suspect tissue 126 requiring evaluation on or near the ovarian surface.

While lumens of many portions of the reproductive system are considerably larger, the lumens 118 of fallopian tubes 114, 116 may only be a millimeter in diameter at their narrowest point.

Typical endoscopes, as used for colonoscopy and upper gastrointestinal tract investigations, are approximately a centimeter in diameter, far too large to pass comfortably through a normal fallopian tube. While bronchoscopes are typically smaller in diameter than colonoscopies, they are typically too large to comfortably pass through fallopian tubes. Further, typical endoscopes offer a visual channel alone.

SUMMARY

A falloposcope is described, as is a method of using the falloposcope to screen a patient for fallopian tube and/or ovarian cancer. The falloposcope has an optical imaging subsystem capable of performing optical and fluorescence imaging, and an optical coherence tomography (OCT) channel, all in a diameter less than 1 millimeter (mm) and in a particular embodiment between 0.7 and 0.8 mm. The method includes inserting the falloposcope through a lumen of vagina, cervix, uterus, and fallopian tube such that a tip of the falloposcope is in proximity to a first fallopian tube or ovary of the patient; providing at least one fluorescence stimulus wavelength through one or more illumination fibers of the falloposcope, while imaging light at one or more fluorescence emission wavelengths through a coherent fiber bundle to form fluorescence emissions images; and determining suspect tissue from the fluorescence emission images. The OCT channel is also used to examine tissue, both to determine suspect tissue and analyze suspect tissue from fluorescence observations.

In an embodiment, a method of observing an object includes emitting light of a first fluorescence stimulus wavelength from a tip of a falloposcope, the tip of the falloposcope in proximity to the object, while imaging light at a first fluorescence emission wavelength, to form at least one first fluorescence emissions image of the object the falloposcope having a body adapted to passage through a lumen of a fallopian tube; imaging the object at the first fluorescence stimulus wavelength to form a first stimulus wavelength image; emitting light of a second fluorescence stimulus wavelength from the tip of the falloposcope while imaging light at a second fluorescence emission wavelength, to form at least one second fluorescence emissions image of the object; imaging the object at the second fluorescence stimulus wavelength to form a second stimulus wavelength image; and determining suspect abnormalities of the object from at least one first fluorescence emission image, at least one second fluorescence emissions image, the first stimulus wavelength image, and the second stimulus wavelength image. In particular embodiments, the object is an ovary or fallopian tube.

In another embodiment, a method of screening an object for an abnormality includes positioning a falloposcope having an optical coherence tomography (OCT) channel through such that a tip of the falloposcope is in proximity to the object; and using the OCT channel to perform optical coherence tomography and determining an abnormality from the optical coherence tomography.

In another embodiment, a falloposcope has an elongated body having a first end and a head end, the head end and elongated body having a diameter of less than one millimeter; an afferent and an efferent optical coherence tomography (OCT) channel having an optical fiber couplable to an OCT apparatus source and interferometer through the elongated body from the first end to an OCT port near the head end, the OCT apparatus comprising a source of coherent light and an interferometer that receives light through the optical fiber from the OCT port. The falloposcope also has an optical, and in some particular embodiments infrared, imaging channel having: an image sensor that is either an electronic camera at the tip end of the body or a combination of a coherent fiber bundle extending from a first end of the bundle near the first end of the body through the body to a lens assembly at the tip end of the body, the lens assembly configured to focus images on an end of the coherent fiber bundle, and an electronic camera coupled to image light received from the coherent fiber bundle, and an illuminator selected from the group consisting of at least one semiconductor light emitting device at the head end of the body and an illumination fiber extending at least from the first end of the body to the head end configured to pass light from an illuminator coupled to the illumination fiber near the first end of the body to the head end of the body. In this embodiment the illuminator is adapted to provide illumination selectable from options including at least visible light, and light of at least a first fluorescence stimulus wavelength; and the electronic camera has at least a mode responsive to a broad spectrum of light and a first fluorescence emissions mode wherein the camera does not respond to light of the first fluorescence stimulus wavelength but does respond to light of a first fluorescence emissions wavelength longer than the first fluorescence emissions wavelength. The camera feeds an image processor, the image processor adapted to control the illuminator and to process images received from the camera.

In another embodiment a falloposcope has an elongated body with circumferential diameter less than one millimeter; an afferent and efferent optical coherence tomography (OCT) channel having an optical fiber extending through the body; an illuminator coupled to an illumination fiber near the first end of the body to the head end of the body to provide illumination The falloposcope also has an image sensor including a lens assembly configured to focus images on an end of the coherent fiber bundle, and an electronic camera coupled to image light received from the coherent fiber bundle, the sensor being mode responsive to a broad spectrum of light and a first fluorescence emissions mode and not responsive to light of the first fluorescence stimulus wavelength; and an image processor adapted to control the illuminator and generate enhanced images from images received by the image processor from the image sensor.

DETAILED DESCRIPTION OF THE EMBODIMENTS

A small diameter steerable endoscope, known herein as a falloposcope, has diameter of less than two millimeters and preferably less than one millimeter, and in a particular embodiment of seven tenths of a millimeter, is capable of being inserted through narrow openings and performing visual inspection of objects to detect abnormalities. In particular, the falloposcope is adapted to be inserted through the natural orifice of the lumens of vagina, uterus, and fallopian tubes to observe objects such as the ovaries and portions of the fallopian tubes, and detect abnormalities such as early stage ovarian cancer. The falloposcope is equipped with multispectral fluorescence imaging (MFI) and optical coherence tomography (OCT).

MFI utilizes endogenous fluorophores (such NADH and tryptophan-rich proteins such as collagen) for contrast. MFI requires a fluorescence stimulus-wavelength light source, together with multiband, wavelength-selective, visual observation apparatus for viewing a targeted ovary at multiple emissions wavelengths. With the use of ultraviolet stimulus wavelengths, between 240 and 400 nanometers (nm) in MFI, it is possible to detect fluorescence due to proteins. Using ratios of the autofluorescence produced at each pixel at each of several stimulus wavelengths and at more than one, discrete emissions wavelength, and using other image processing techniques, combined false-color images having significantly enhanced contrast of lesions are generated. The combined false-color images are presented to the surgeon to permit location of suspected tissue abnormalities for which further investigation by single-point OCT is performed. In some instances where sufficient abnormalities of tissue are seen under MFI, further investigation by laparoscopic biopsy or other techniques may be advised.

OCT uses near-infrared light to build up cross sectional images up to about 2 millimeters (mm) deep in tissue with about 3-20 micron (μm) resolution. It is anticipated that OCT will be performed at planned viewing locations, as well as locations where the surgeon sees suspect tissues in the combined MFI images, and where the surgeon sees suspect tissues in optical images.

The falloposcope is also capable of obtaining optical images when visible light illumination is provided, such that the surgeon may use such optical images to guide insertion and manipulation of the falloposcope to position the falloposcope head at particular observation points. In addition to performing MFI and OCT at preplanned observation points, suspect tissues seen in optical images obtained while positioning the falloposcope head may also be inspected with MFI and/or OCT modes as deemed necessary by the surgeon.

Experiments have shown that MFI and OCT observations can distinguish between normal and cancerous tissue in ex vivo human ovarian and fallopian tube surgical samples.

System Characteristics

Figure 2:
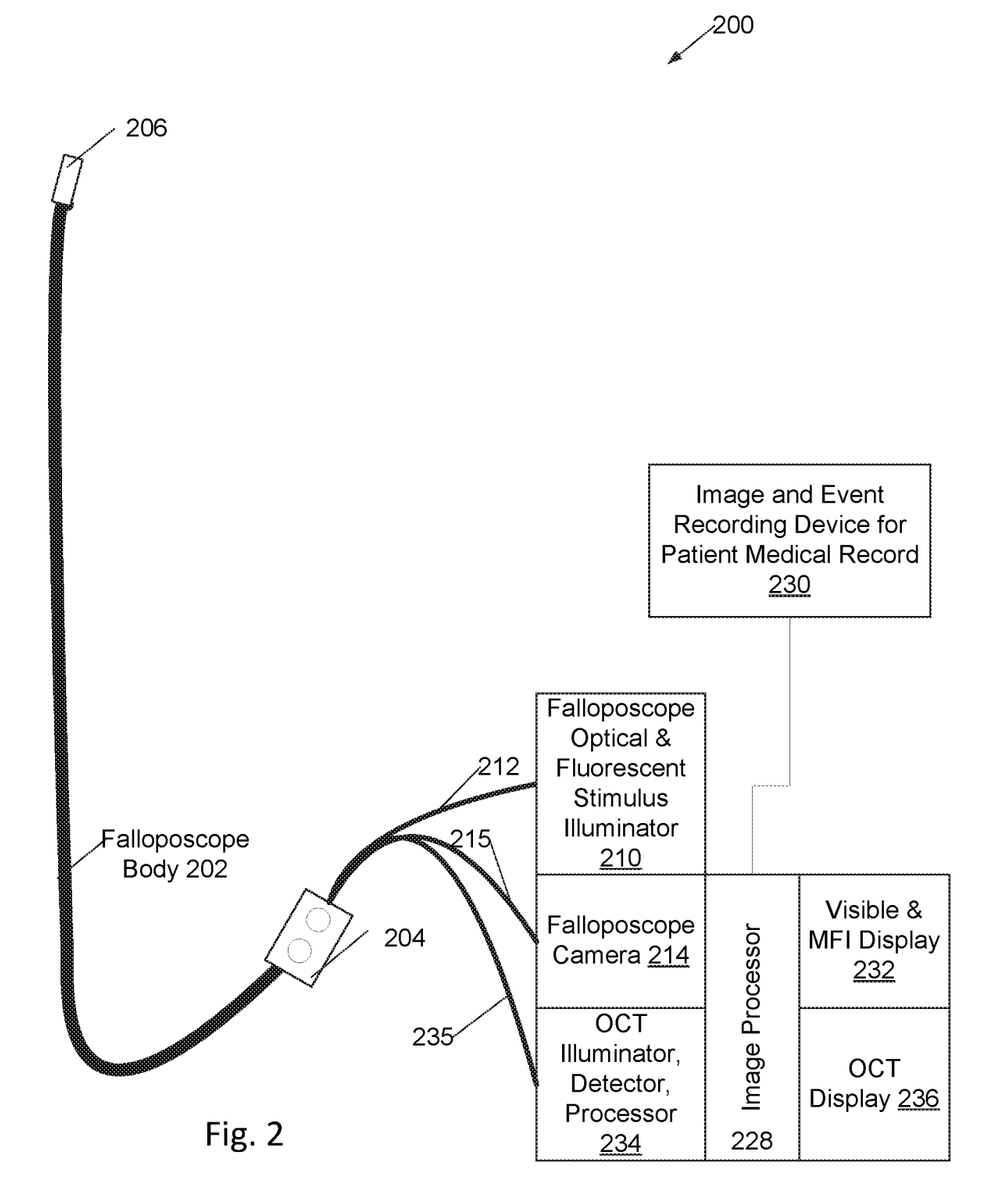
FIG. 2 is a schematic diagram of one falloposcope, in an embodiment.

The falloposcope system 200 is illustrated in FIG. 2. A falloposcope body 202 extends from a proximal end steering handle 204 to a distal-end falloposcope head or tip 206; body 202, as detailed in FIG. 3A, is formed from one or more steering wires 352 slideably disposed in steering wire tubes 354 but fixed to the tip as pull wires (detailed as 310 in FIG. 3), at least one MFI illumination fiber 212, an MFI coherent imaging fiber bundle 215, and OCT stimulus and sensing fiber 235 wrapped in a moisture-resistant biocompatible sheathe; in an embodiment the sheathe is formed of stainless steel with a PTFE (polytetrafluoroethylene) lining; in an alternative embodiment the sheathe is formed of at least one layer 362 of braided polymer fiber over a PTFE lining 364, the polymer fiber selected from a biocompatible fiber such as Pebax, Nylon, FEP, PTFE composites, and polyimide (PI). In alternative embodiments, a MFI illumination fiber bundle is as MFI illumination fiber 212.

An optional connector (not shown) may be located between steering handle 204 and illuminator 210, camera 214, and OCT illuminator-detector 234 for convenience of setup and operation. This connector would divide stimulus fiber 212, coherent fiber bundle 215, and OCT fiber 235 into two portions mating at the connector.

Figure 4:
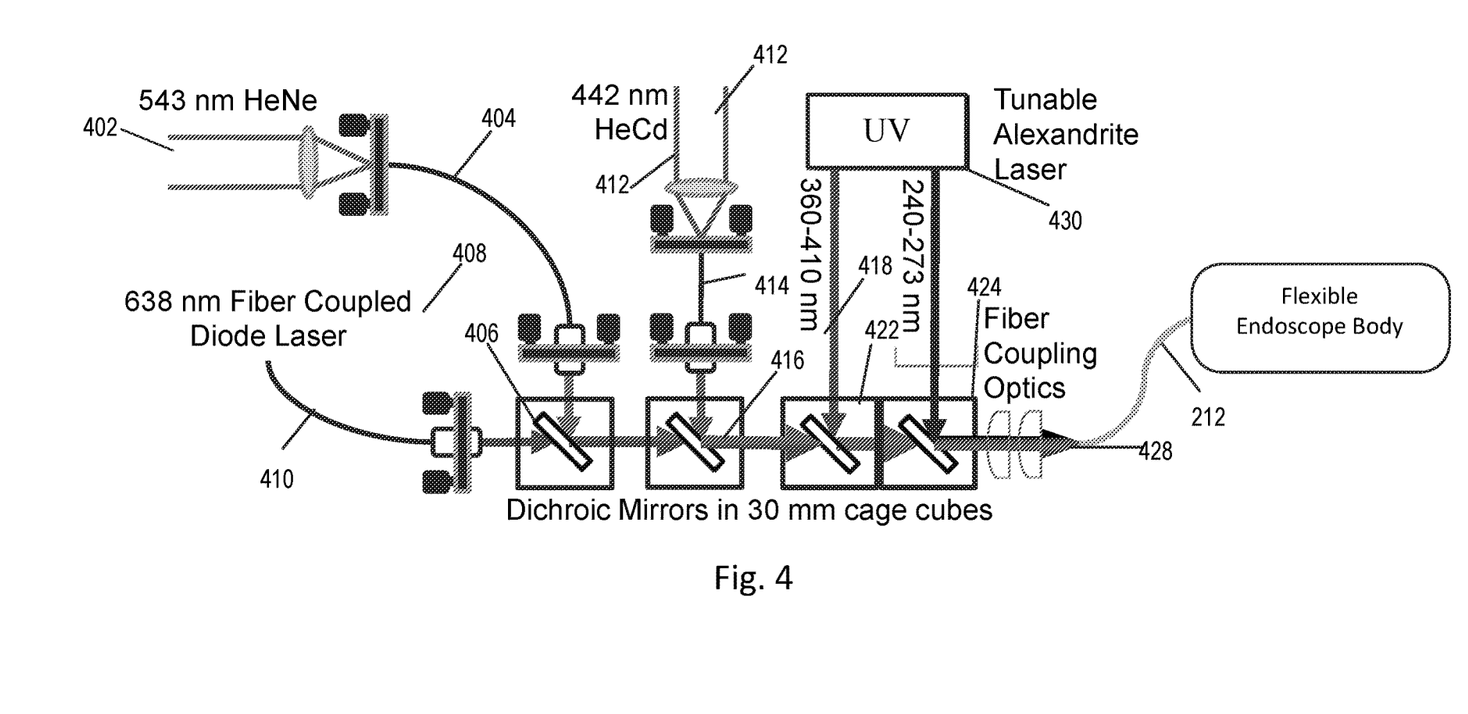
FIG. 4 is a schematic diagram of an illuminator for multispectral fluorescence imaging (MFI).

The MFI illumination fiber 212 couples at its proximal end to a laser-based illumination device such as that illustrated in FIG. 4. The laser-based illumination device has illuminator 210 (FIG. 2) with separate laser sources for each fluorescence imaging wavelength, and an actual stimulus wavelength in use at a given instant of time is determined by an active laser. In illuminator 210, for example, light 402 (FIG. 4) from a 543 nm helium-neon laser is brought through an optical fiber 404 to a first combiner 406 having a dichroic mirror reflective to 543 nm light, the first combiner 406 combines this light with 638 nm light 408 received over a fiber 410 from a semiconductor laser. Light 412 from a 442 nm laser received over a fiber 414 is combined in a second combiner 416 with light from the first combiner. Similarly, light 418 of 360-400 nm and light 420 of 240-265 nm is combined with light from the second combiner in a third 422 and fourth 424 combiner. A composite beam from all these lasers is coupled by coupling optics 428 into MFI illumination fiber 212 of falloposcope body 202.

The falloposcope 200 also has an image processor 228 coupled to receive images from the hysteroscope camera 224; this processor can provide raw and enhanced images, including enhanced images generated from ratios of reflected light and fluorescence emissions light images and from multiple stimulus wavelengths, on display 232. The multispectral fluorescence imaging (MFI) portion of the falloposcope uses specific fluorescence excitation (or stimulus) wavelengths as generated by lasers of illuminator 210 (FIG. 2) to illuminate tissue of the patient. Light received from the tissue by lens 308 into coherent fiber bundle 215 is imaged through a filter-changer and electronic camera in falloposcope camera 214.

Each stimulus wavelength is paired with one or more emission band wavelengths; each paired emission band wavelength includes wavelengths longer than the associated stimulus wavelength and excludes the stimulus wavelength itself. For each emission wavelength band, an emissions filter in the filter changer (not shown) of the falloposcope camera 214 is provided having a passband coinciding with the emissions band, the emissions filter having a stop-band or notch that excludes light at the associated stimulus wavelength. Fluorescence emissions images are acquired by activating a laser of illuminator 210 to provide stimulus wavelength light, while imaging through the paired emissions filter.

Falloposcope camera 214 also is adapted to acquire reflected light images by activating a laser of illuminator 210 to provide light, while imaging through a neutral-density filter or a clear filter. The fluorescence data provides molecular concentration information about the tissue and the reflected light data provides absorption information about the tissue.

Images captured with the falloposcope camera 214 are provided to a digital image processor 228. Using data processing techniques—including for example Mahalanobis distance, Linear Discriminant Analysis, Quadratic Discriminant analysis and Logistic Regression—tissue disease state can be discriminated with high accuracy. The image processor uses the captured image data create false color images and present these false color images to the surgeon on display 232 with enhanced visual contrast between tissue states.

In a particular embodiment, excitation or fluorescence stimulus wavelengths used for fluorescence imaging used in the analysis are 255, 280, 320, 340, 370, 400, 440, 480, and 550 nm, each ±5 nm. In a particular embodiment, the system records MFI fluorescence emissions images in emission bands of 345-410, 375-410, 410-500, 500-600, and 600-655 nm. In other embodiments it is anticipated that between 4 and 6 stimulus wavelengths are provided each of which lies in the range from 220 to 600 nm.

In experimentation, ex vivo ovarian tissue was imaged using the fluorescence excitation and emission combinations in Table 1 below. Additionally the tissue was imaged with reflected light at 370, 400, 415, 440, 480 and 555 nm. Quadratic discriminant analysis on subsets of the 12 fluorescence images and 6 reflected light images produced 56 subsets of the image type measurements with perfect discrimination of tissue as normal, cancerous and benign conditions on 47 ovarian tissue samples. Further analysis produced an additional 1256 subsets that only failed to classify the state of one of the 47 tissue samples.

During experimentation with MLR and QDA models, image-types with excitation or emission wavelengths at or around the hemoglobin absorption peaks and troughs generally showed good tissue-type discrimination. Image-types R400 and R415, both sampling the blue side of the blood absorption peak, were included in over 92% of good QDA subsets. The illumination wavelengths of 440 and 480 nm were found in both the fluorescence and reflectance MLR models as the best predictors of tissue pathology. The process of determining variables for MLR models eliminated image-types with high covariance and thus redundant information. Since 440 nm is near the deoxyhemoglobin absorption peak while 480 nm is in a trough, the image-types acquired with these illumination wavelengths may present the strongest and weakest effects of blood absorption respectively in these samples.

Of the fluorescence image-types, F480 (fluorescent emissions at 520-655 nm when stimulated at 480 nm) was determined a strong discriminator by MLR and most frequently occurred in good QDA subsets. Unlike the other wavelengths with strong discrimination between pathology, the excitation and emission band of F480 are expected to have relatively low influence from blood absorption. The fluorescence from F480 has been shown to be higher for normal than cancer tissue in previous fiber probe studies, due to the primary excited fluorophores of FAD and collagen.

TABLE 1

| MFI excitation-emission wavelength pairs | |
|---|---|
| Excitation | Emission |
| 280 nm | 345 nm-410 nm |
| 320 nm | 375 nm-410 nm |
| 320 nm | 410 nm-500 nm |

TABLE 1-continued

MFI excitation-emission wavelength pairs

| Excitation | Emission |
|---|---|
| 340 nm | 375 nm-410 nm |
| 340 nm | 410 nm-500 nm |
| 370 nm | 410 nm-500 nm |
| 400 nm | 600 nm-655 nm |
| 440 nm | 500 nm-600 nm |
| 440 nm | 600 nm-655 nm |
| 480 nm | 520 nm-600 nm |
| 480 nm | 600 nm-655 nm |
| 550 nm | 600 nm-655 nm |

In a particular embodiment, stimulus illuminator 210 provides a first wavelength, while camera 214 captures a first emissions wavelength image, and continues providing the first wavelength while camera 214 captures a first reflected light image. Then, stimulus illuminator 210 provides a second wavelength, while camera 214 captures a second emissions wavelength image, and continues providing the second wavelength while camera 214 captures a second reflected light. The stimulus and emissions wavelength pairs are selected from those in Table 1. The image processor 228 then uses all 4 of these images to determine suspect abnormal tissue. In alternative embodiments, additional images are captured using one or more additional stimulus wavelength/emissions wavelength pairs from Table 1, and in a particular embodiment all 12 stimulus wavelength/emissions wavelength pairs of table 1 are used.

Proximal Optics

The proximal optics of the falloposcope system includes an OCT illuminator detector and processor 234 (FIG. 2) for OCT illumination and detection; and apparatus the illuminator 210 and camera 214 for MFI illumination and detection. The OCT illuminator, detector, and processor 234 is a spectral domain system with a center wavelength of 890 nm and bandwidth of 150 nm; this OCT illuminator, detector, and processor 234 includes a source (FIG. 2) of coherent light operating at the center wavelength, this source is coupled through a fiber 235 to the OCT port 506 (FIG. 5) and thence to tissue. OCT illuminator detector and processor 234 also includes an interferometer that receives light both from the source and through fiber 235 and the OCT port from tissue, OCT results are displayed on OCT display 236.

In an embodiment, the MFI operates multiple stimulus or excitation wavelengths provided by illuminator 210 (FIG. 4) to selectively generate one of five wavelengths (250, 375, 442, 543, and 638 nm) from four lasers into a 100 µm core fiber 215 that brings the light to the tip 206 of the falloposcope. A custom built pulsed Alexandrite laser 430 supplies excitation wavelengths between 240 and 400 nm, and other lasers provide 445, 535, and 638 nm wavelength (see description of stimulus illuminator 210 above). Fluorescence emissions from 375 nm-650 nm and reflected light collected by the fiber bundle 215 in the distal falloposcope tip 206 are brought through a receive filter-changer (not shown) in falloposcope camera 214, see description of falloposcope camera 214 above. By selecting excitation wavelength and using appropriate emission filters, the falloposcope is tuned to particular chromophores and fluorophores of interest, some of which are associated with abnormal tissues.

Distal Optics and Mechanics

Figure 3:
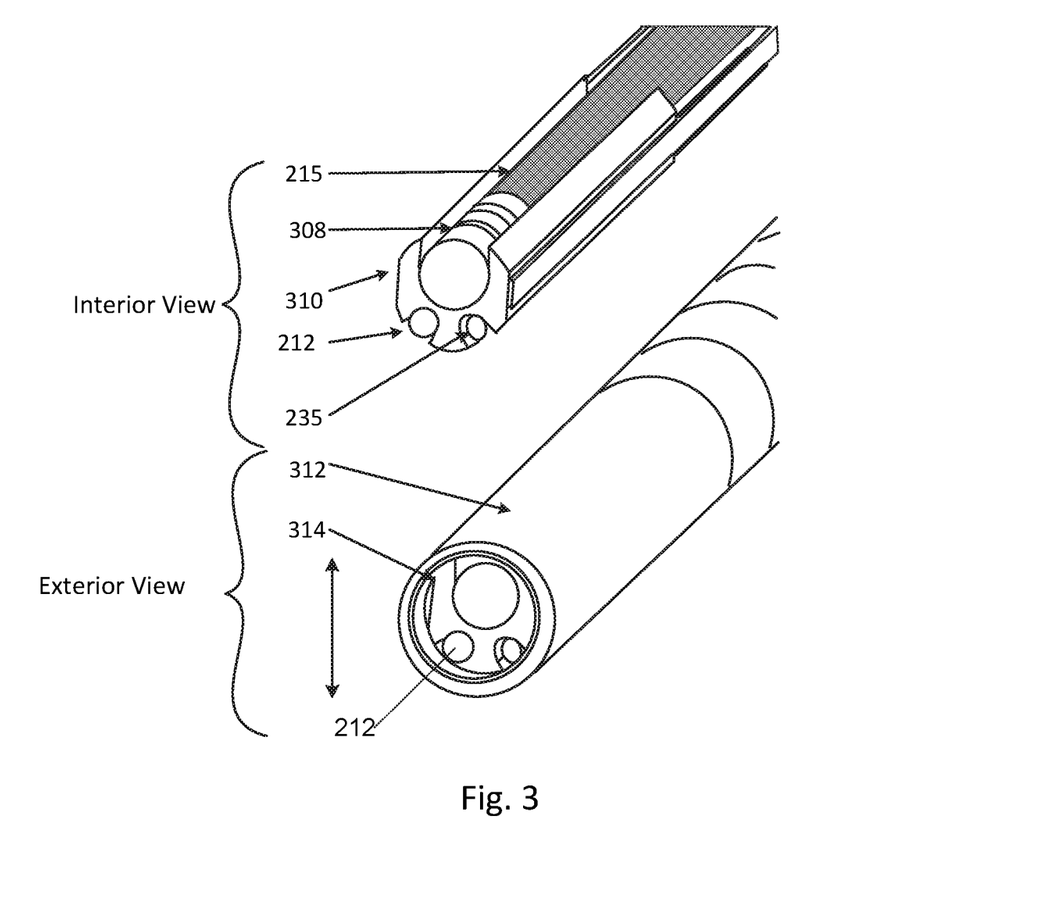
FIG. 3 is a schematic diagram of a distal end of the falloposcope.
Figure 3A:
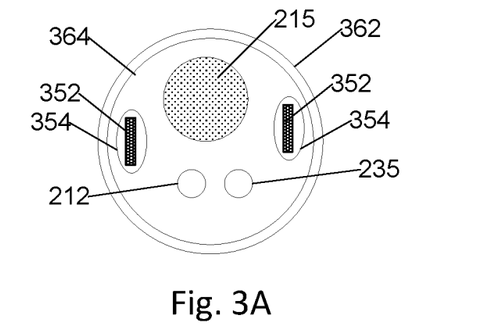
FIG. 3A is a cross sectional schematic diagram of a cross section of the falloposcope at mid-shaft.
Figure 5:
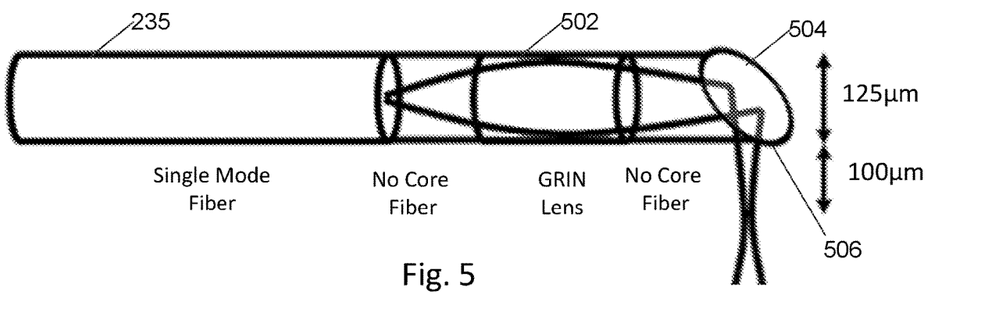
FIG. 5 is a schematic diagram of the optical coherence tomography (OCT) side-scanning optics of the distal end of an embodiment of the falloposcope.
Figure 6:
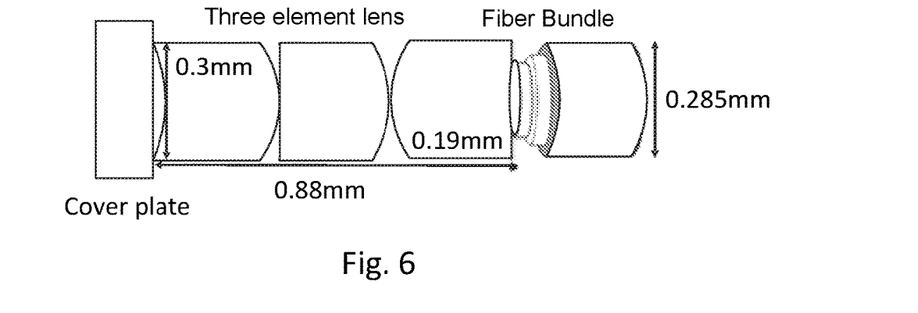
FIG. 6 is a schematic diagram of the multispectral fluorescence imaging (MFI) optics of the distal end of the falloposcope.

The distal end of a particular embodiment of the falloposcope as shown in FIG. 3 combines an imaging fiber 235 for OCT, an illumination fiber 212 for MFI, a 3,000 element 285 µm diameter coherent fiber bundle 215 for imaging and an associated micro-objective lens 308 (as shown in FIG. 6), as well as steering wires 310 for steering the tip. With custom designed optics, this achieves a full field of view of 70° at working distances of 3 to 10 mm. The distal tip of the OCT fiber 235 is lensed with GRIN lens 502 and angle polished with mirror 504 to achieve side-viewing OCT, as shown in shown in FIG. 5. A pair of steering wires 310 is provided to enable the falloposcope tip to bend approximately 60° to enable insertion through the fallopian tubes as well as to permit visualizing the fimbriae and ovary, and to permit placing the OCT channel in contact with tissue to be examined. In alternative embodiments, the OCT channel is forward viewing instead of side-viewing. In alternative embodiments, coherent fiber bundle 215 has a different, preferably greater than 3000, element count.

The falloposcope tip of FIG. 3 has a stainless steel tubular portion 312 and a transparent distal window 314 through which imaging is performed. In an alternative embodiment, stainless steel is replaced with a plastic.

OCT

The MFI ratiometric images from the MFI image processor 228 indicate regions of interest for further examination by OCT. OCT provides high resolution subsurface information of tissue microstructure permitting more precise diagnosis. The approximately 20 to 100 µm thick epithelial lining of the Fallopian tubes and ovaries should be examined for optimum cancer detection. The OCT system is designed to be side viewing and provides its highest lateral resolution at the epithelium.

The proximal OCT system is a Spectral Domain (SD-OCT) OCT system used previously with other dual modality endoscopes. The OCT has an 890 nm superluminescent diode source with full width half maximum bandwidth of 150 µm. According to the equation $\Delta z = (2 \ln 2/\pi)*(\lambda\_0^2/\Delta\lambda)$ this corresponds to a theoretical axial resolution of 2.3 µm in air and in practice achieves sub 5 µm axial resolution in tissue. The OCT system can acquire OCT images at a rate of 4000 A-scans/s. Light from the OCT source is carried through the falloposcope by a 780HP single mode fiber 235 selected for a cut-off wavelength lower than the OCT system shortest wavelength and with a 125 µm or less cladding diameter.

The distal OCT optics as illustrated in FIG. 5 and described above are designed to achieve sub-10 µm resolution at a 100 µm depth while matching the 125 µm cladding diameter of the fiber.

Method of Use

Figure 7:
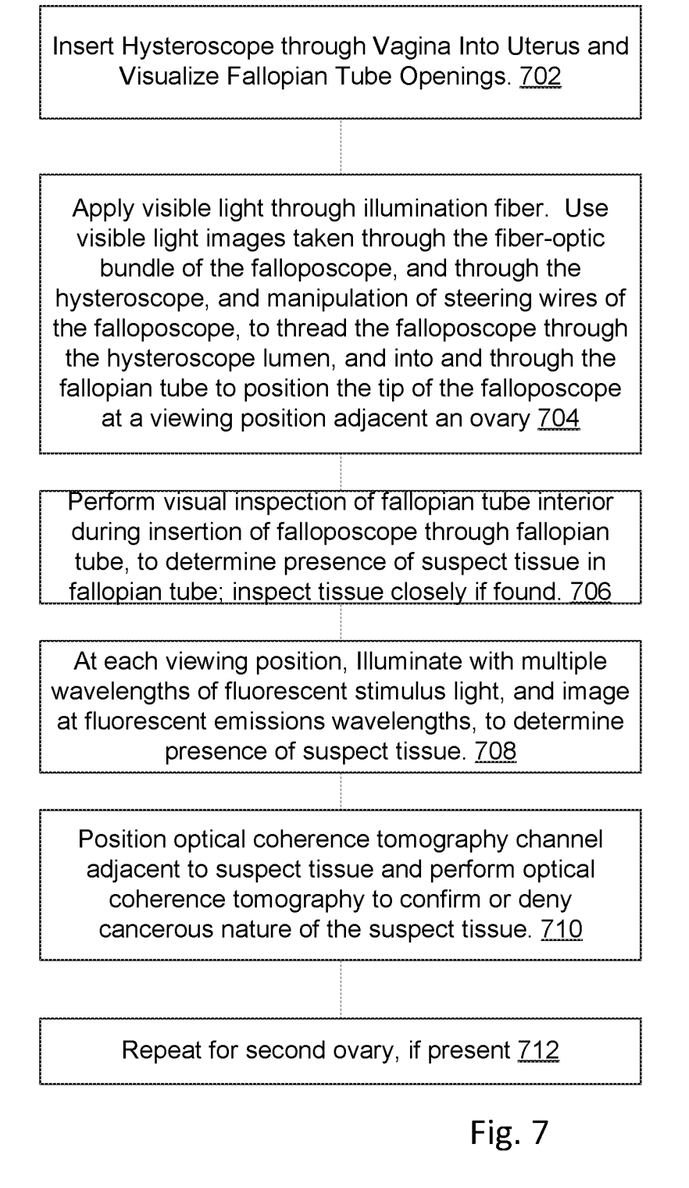
FIG. 7 is a flowchart of use of the falloposcope to screen a patient.
Figure 8:
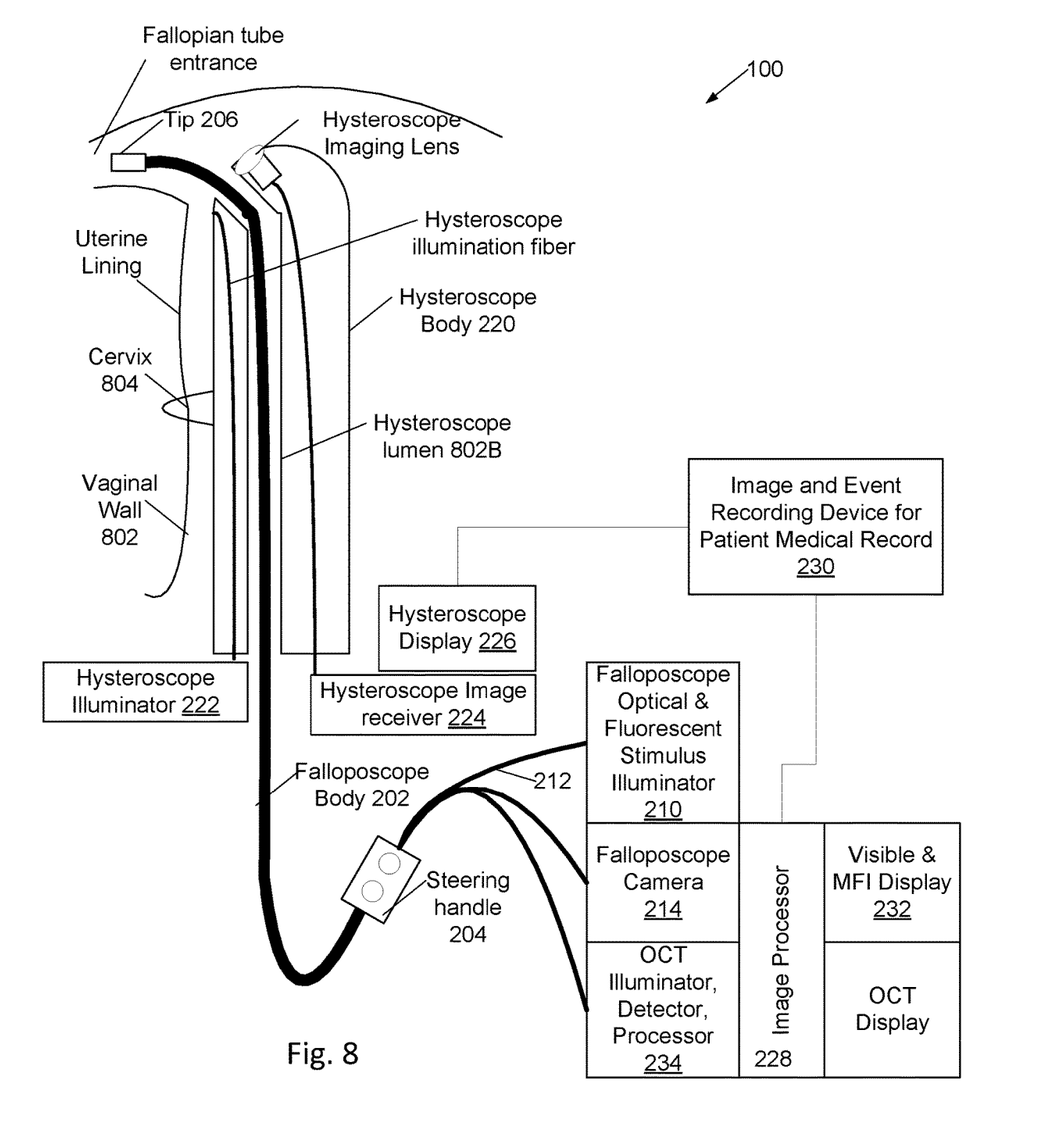
FIG. 8 is a schematic block diagram of a hysteroscope and falloposcope for use in examining a patient's ovaries and fallopian tubes, showing insertion of the falloposcope into the fallopian tube.
Figure 10:
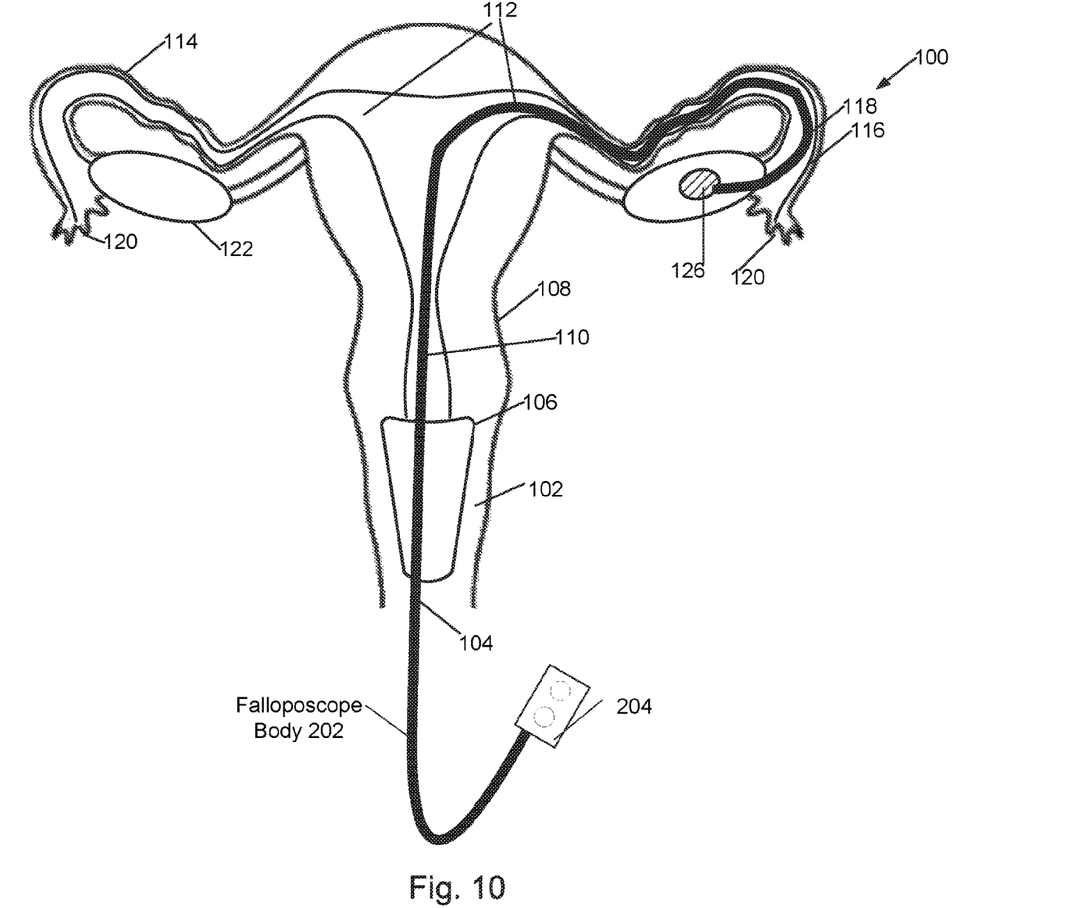
FIG. 10 illustrates a falloposcope in position for imaging abnormal tissue of an ovary.

A method of using the falloposcope is outlined in FIG. 7, with reference to FIGS. 2 and 8. Falloposcope 200 is used with a hysteroscope 220 (FIG. 8), a hysteroscope illuminator 222, a hysteroscope camera 224, and a hysteroscope display 226 to assist in positioning the falloposcope into an operational position such as that illustrated in FIG. 10.

The hysteroscope 220 is inserted 704 through vagina 802 and cervix 804 into the uterus and the fallopian tube entrance is located as shown in FIG. 8. The falloposcope distal tip 206 is threaded 704 under visual guidance through the vagina, cervix, and uterus, and thence into and through the fallopian tube. Direct visual guidance is achieved through the falloposcope distal tip by providing visible-light or multiple wavelengths of stimulus light illumination through the MFI illumination fiber and performing visible-light optical imaging through the fiber bundle 215 (FIG. 2, 3). In order to facilitate navigation of the slender and relatively flexible falloposcope through the relatively wide lumens of vagina, cervix, and uterus and thus into the fallopian tube, and since imaging through the fiber bundle is of limited resolution; additional imaging for guidance of the falloposcope through vagina, cervix, and uterus to the mouth of the fallopian tube is performed with a hysteroscope 220. In a particular embodiment, the narrow falloposcope is threaded through a lumen 802B of larger-diameter hysteroscope 220 as illustrated in FIG. 8, the hysteroscope being positioned with hysteroscope tip adjacent to the fallopian tube entrance, and the falloposcope being inserted through the hysteroscope into the fallopian tube. The distal end of the falloposcope is threaded through the fallopian tube and positioned in proximity to a first ovary of the patient. The tip of the falloposcope is manipulated, through rotation of the falloposcope, through tweaking knobs of steering handle 204 to tension the steering wires 310 to bend or straighten the tip 206, and through further insertion or partial extraction of the falloposcope body 202, to several viewing positions. The steering wires 352 are coupled to manipulation controls on a steering handle 204 similar to the manipulation controls of conventional endoscopes.

During insertion and positioning of the falloposcope, images obtained through the fiber bundle are presented on display 236 to the surgeon manipulating the falloposcope. While one purpose of these images is to allow navigation and positioning of the falloposcope head, these images also permit the surgeon to perform an optical inspection 706 of such areas as the interior of the fallopian tube and parts of the fimbriae, as well as portions of the ovary. If any suspect abnormalities, such as potentially cancerous tissues, are seen, insertion of the falloposcope is paused to permit further investigation of the suspect tissues using MFI fluorescence imaging and/or OCT optical coherence tomography; once this investigation is complete, insertion continues to the desired viewing position.

At each desired viewing position, light at a selected stimulus wavelength is emitted 708 through the MFI illumination fiber 212. While this stimulus wavelength light is being provided, fluorescence emission light is received through the fiber bundle and thence through a selected receive filter opaque to the stimulus wavelength, but transparent to at least one emission wavelength longer than the stimulus wavelength; this light is imaged to form an emission wavelength image. The received light filter is then changed to a clear or a neutral density filter and a reflected-light image is obtained. The emission wavelength image and reflected light images are processed by the image processor 228 to determine locations of any suspect tissue on the ovary, within the fimbriae, or within the fallopian tube.

In embodiments, at each viewing location, light at one or more additional stimulus wavelengths selected from the wavelengths of Table 1 and provided by the proximal optics are provided in a sequence, while the receive filter is changed so light at a second or additional emissions wavelength is imaged, to provide additional emission wavelength images. Determination of suspect tissue may be based upon one or more of the emission wavelength images obtained at each position, or on all emission wavelength images. In alternative embodiments, additional stimulus wavelength sources and paired receive filters are provided to allow additional stimulus wavelength—emissions imaging wavelength pairs.

In the event suspect abnormalities tissue is found, the tip is further manipulated to place 710 the GRIN lens of the OCT channel in contact with the tissue to be examined, and optical coherence tomography is performed.

Once study of the first ovary is completed, the method is repeated 712 for the second ovary of the patient. Throughout the procedure, images taken in both visible light and in fluorescence emissions light through the falloposcope camera 214, and images obtained through the hysteroscope 220 in embodiments using a hysteroscope, and OCT data are recorded in an image and event recording system for placement into the patient's medical record.

Figure 9:
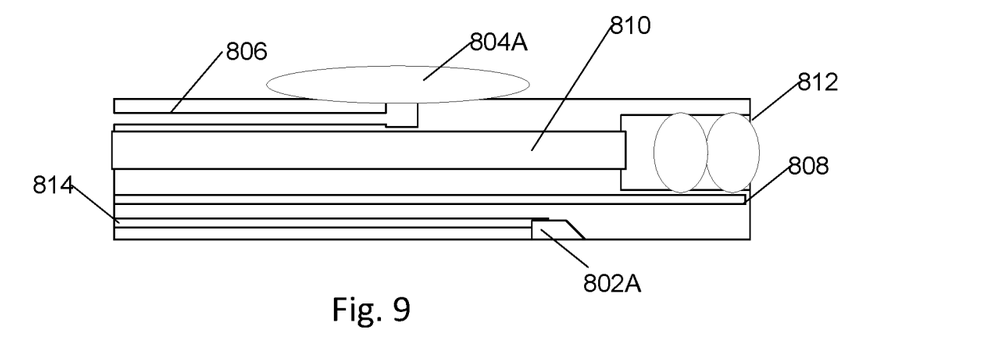
FIG. 9 is a cross sectional diagram of a falloposcope tip equipped with an everting balloon for use in positioning the falloposcope tip.

In an alternative embodiment, the falloposcope tip is fitted with an everting balloon as illustrated in FIG. 9. In use, when it is desired to ensure that the OCT port 802A is adjacent to suspect tissue, balloon 804A is inflated through a lumen 806 to press the tip against tissue. Also shown in FIG. 9 is the MFI illumination fiber 808, the coherent bundle for MFI imaging 810, an MFI lens system 812, and the OCT fiber 814.

In an alternative embodiment, instead of the external laser-based illuminator 210 shown in FIG. 4, one or more light-emitting semiconductor devices are incorporated directly into falloposcope tip and energized through a wire when light emission from the tip is desired. In embodiments, the light-emitting semiconductor devices are laser diodes, in an alternative embodiment the light-emitting semiconductor devices are light-emitting diodes.

In an alternative embodiment, instead of using a coherent fiber bundle to route images from falloposcope tip to a filter and camera located outside the patient, an electronic camera is fabricated within the falloposcope tip to capture images. In a particular embodiment, the electronic camera within the falloposcope tip has a lens adapted to focus images on a hyperspectral photosensor array, the hyperspectral photosensor array having a filter layer incorporating a tiling pattern of microfilters, with each microfilter located over a photosensor of the array, in manner similar to Bayer-pattern photosensors but with pass bands at selected fluorescence emissions wavelengths and stimulus wavelengths instead of at red, green, and blue wavelengths as with standard Bayer-pattern devices. In a particular embodiment, the hyperspectral photosensor array has a pattern of filters with passbands of 375-410 nm, 410-500 nm, 500-600 nm, 600-655 nm, and a clear filter. This embodiment is capable of performing observations at the same stimulus wavelength-emissions wavelength pairs discussed with reference to Table 1.

In another alternative embodiment, instead of a coherent fiber bundle having round or rectangular cross section with a fixed imaging lens at the falloposcope tip adapted to focus received light as images on the end of the coherent fiber bundle as previously discussed; a lens system adapted to receive light from the falloposcope tip is equipped with scanning apparatus, such as one or more mirrors deflected by piezoelectric transducers, adapted to perform a raster or line scan of an image onto a single fiber or linear coherent fiber bundle.

In yet another alternative embodiment, prior to inserting the falloposcope, a guide-wire is inserted into the uterus of the patient leading to the fallopian tube entrance. The falloposcope is fabricated with a lumen sufficiently large to fit over the guide wire, and is then inserted over the guide wire into the fallopian tube entrance.

Combinations

The falloposcope herein described, and its method of use, may be made using various combinations of features, some of which are detailed below.

A method designated A of observing an object includes emitting light of a first fluorescence stimulus wavelength from a tip of a falloposcope, the tip of the falloposcope in proximity to the object, while imaging light at a first fluorescence emission wavelength, to form at least one first fluorescence emissions image of the object the falloposcope having a body adapted to passage through a lumen of a fallopian tube; imaging the object at the first fluorescence stimulus wavelength to form a first stimulus wavelength image; emitting light of a second fluorescence stimulus wavelength from the tip of the falloposcope while imaging light at a second fluorescence emission wavelength, to form at least one second fluorescence emissions image of the object; imaging the object at the second fluorescence stimulus wavelength to form a second stimulus wavelength image; and determining suspect abnormalities of the object from at least one first fluorescence emission image, at least one second fluorescence emissions image, the first stimulus wavelength image, and the second stimulus wavelength image.

A method designated AA including the method designated A, wherein the falloposcope tip has a diameter of less than one millimeter, and the falloposcope is adapted for insertion of its tip through a lumen of a fallopian tube.

A method designated AB including the method designated A or AA, wherein imaging light at a first fluorescence emission wavelength is performed through a lens and a coherent fiber bundle of the falloposcope.

A method designated AC including the method designated A, AA, or AB, wherein generating light of the first stimulus wavelength is performed by providing light from a laser through a stimulus light fiber of the falloposcope.

A method designated AD including the method designated A, AA, or AB wherein emitting light of the first stimulus wavelength is performed by energizing a light emitting semiconductor device located near the falloposcope tip.

A method designated AE including the method designated A, AA, AB, AC, or AD further including placing an optical coherence tomography (OCT) channel of the falloposcope adjacent the suspect abnormalities and performing optical coherence tomography to further analyze the suspect abnormalities.

A method designated AF including the method designated A, AA, AB, AC, AD, or AE wherein the step of inserting a falloposcope through a lumen is performed by observing the falloposcope and a portion of lumen with a hysteroscope.

A method designated AG including the method designated AF, further including inflating an everting balloon to aid positioning the OCT channel adjacent the suspect abnormalities.

A method designated AH including the method designated A, AA, AB, AC, AD, AE, AF, or AG, further comprising using a steering wire controlled by a knob on a steering handle to help position the falloposcope tip.

A method designated AI including the method designated A, AA, AB, AC, AD, AE, AF, AG or AH, further comprising inserting a guide wire through the lumen to a determined position, and inserting the falloposcope over the guide wire.

A method designated AJ including the method designated A, AA, AB, AC, AD, AE, AF, AG, AH or AI wherein positioning the falloposcope tip near an object comprises inserting the falloposcope through lumens of vagina, cervix, uterus, and fallopian tube such that the falloposcope tip is in proximity to a first fallopian tube or ovary of a patient, wherein the observed object is the first fallopian tube or ovary of the patient, and wherein the suspect abnormalities are tissue of the fallopian tube or ovary having characteristics consistent with cancerous tissue.

A method of screening an object designated D for an abnormality includes positioning a falloposcope having an optical coherence tomography (OCT) channel through such that a tip of the falloposcope is in proximity to the object; using the OCT channel to perform optical coherence tomography and determining an abnormality from the optical coherence tomography.

A method of screening an object designated DA including the method designated D, wherein the step of positioning a falloposcope such that a tip of the falloposcope is in proximity to the object is performed by observing the falloposcope and an opening with a hysteroscope.

A method designated DB including the method designated D or DA, further including inflating an everting balloon to aid positioning the OCT channel adjacent the object.

A method designated DC including the method designated D, DA, or DB, further including using a steering wire controlled by a knob on a steering handle to help position the falloposcope tip.

A method designated DD including the method designated D, DA, DB, or DC further comprising inserting a guide wire through a lumen to a determined position, and inserting the falloposcope over the guide wire.

A method designated DE including the method designated D, DA, DB, DC, or DD wherein positioning the falloposcope tip near an object comprises inserting the falloposcope through lumens of vagina, cervix, uterus, and fallopian tube such that a tip of the falloposcope is in proximity to a first fallopian tube or ovary of the patient, wherein the object is the first fallopian tube or ovary of the patient, and the abnormality is tissue of the fallopian tube or ovary having characteristics consistent with cancerous tissue.

A falloposcope designated B includes an elongated body having a first end and a head end, the head end and elongated body having a diameter of less than one millimeter; an afferent and efferent optical coherence tomography (OCT) channel having optical fiber coupleable to an OCT apparatus source and interferometer through the elongated body from the first end to a side-looking OCT port near the head end, the OCT apparatus comprising a source of coherent light and an interferometer that receives light through an optical fiber from the OCT port; an optical imaging channel having: an image sensor selected from the group consisting of an electronic camera at the head end of the body and a coherent fiber bundle extending from a first end of the bundle near the first end of the body through the body to a lens assembly at the head end of the body, the lens assembly configured to focus images on an end of the coherent fiber bundle, and an electronic camera coupled to image light received from the coherent fiber bundle; and an illuminator selected from the group consisting of at least one semiconductor light emitting device at the head end of the body and an illumination fiber extending at least from the first end of the body to the head end configured to pass light from an illuminator coupled to the illumination fiber near the first end of the body to the head end of the body. The illuminator is adapted to provide illumination selectable from options including at least visible light, and light of at least a first fluorescence stimulus wavelength; wherein the electronic camera has at least a mode responsive to a broad spectrum of light and a first fluorescence emissions mode wherein the camera does not respond to light of the first fluorescence stimulus wavelength but does respond to light of a first fluorescence emissions wavelength longer than the first fluorescence emissions wavelength; and an image processor, the image processor adapted to control the illuminator and to process images received from the camera.

A falloposcope designated BA including the falloposcope designated B, further includes a hysteroscope, the hysteroscope having a body and an optical system with a hysteroscope illuminator adapted to provide light near a first end of the hysteroscope body, a hysteroscope camera adapted to image objects near the first end of the hysteroscope body and to provide images to a display coupled to a second end of the hysteroscope body, and a lumen extending through the hysteroscope body to the first end of the hysteroscope body; wherein the falloposcope of claim 16 extends through the lumen of the hysteroscope body.

A falloposcope designated BB including the falloposcope designated B or BA wherein the illuminator is further adapted to emit light of at least a second fluorescence stimulus wavelength, the second stimulus wavelength different from the first fluorescence stimulus wavelength.

A falloposcope designated BC including the falloposcope designated B, BA, or BB wherein the electronic camera has a second fluorescence imaging mode wherein the camera does not respond to light of the second fluorescence stimulus wavelength but does respond to light of a second fluorescence emissions wavelength longer than the second fluorescence emissions wavelength.

A falloposcope designated BD including the falloposcope designated B, BA, BB, or BC, further including a steering wire configured to bend the elongated body near the head end of the elongated body upon manipulation of a control attached to a manipulation handle of the falloposcope.

A falloposcope designated BE including the falloposcope designated B, BA, BB, BC, or BD, wherein the image processor is adapted to use images obtained from the camera in the first fluorescence emissions wavelength and images obtained from the camera in broad spectrum mode to determine suspect abnormalities viewed in the images.

A falloposcope designated BF including the falloposcope designated B, BA, BB, BC, BD, or BE, further comprising an everting balloon.

A falloposcope designated BG including the falloposcope designated B, BA, BB, BC, BD, or BE, wherein the image processor is further adapted to use optical coherence tomography data acquired through the OCT apparatus to evaluate tissue adjacent the OCT port.

A falloposcope designated C including an elongated body having circumferential diameter less than one millimeter; an afferent and efferent optical coherence tomography (OCT) channel having an optical fiber extending through the elongated body; an illuminator coupled to an illumination fiber near the first end of the body to the head end of the body to provide illumination selectable between ultraviolet and visible light and at least a first fluorescence stimulus wavelength; an image sensor including a lens assembly configured to focus images on an end of a coherent fiber bundle running through the elongated body, and an electronic camera coupled to image light received from the coherent fiber bundle, the sensor being mode responsive to a broad spectrum of light and a first fluorescence emissions mode and not responsive to light of the first fluorescence stimulus wavelength; and an image processor adapted to control the illuminator and generate enhanced images from images received by the image processor from the image sensor.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of observing an object comprising:
    emitting light of a first fluorescence stimulus wavelength from a tip of a falloposcope, the tip of the falloposcope in proximity to the object, while imaging light through a micro-objective lens at a first fluorescence emission wavelength, to form at least one first fluorescence emissions image of the object, the falloposcope having a body adapted to passage through a lumen of a fallopian tube;
    imaging the object through the micro-objective lens at the first fluorescence stimulus wavelength to form a first stimulus wavelength image;
    placing an optical coherence tomography (OCT) channel of the falloposcope adjacent the object and performing optical coherence tomography to further analyze the suspect abnormalities, the OCT channel not using the micro-objective lens and having a lens different from the micro-objective lens; and
    determining suspect abnormalities of the object from at least one first fluorescence emission image, the first stimulus wavelength image, and the optical coherence tomography;
    wherein the falloposcope tip has a diameter of less than one millimeter, and the falloposcope is adapted for insertion of its tip through a lumen of a fallopian tube.

2. The method of claim 1, wherein imaging light at a first fluorescence emission wavelength is performed through the micro-objective lens and a coherent fiber bundle of the falloposcope.

3. The method of claim 1, wherein generating light of the first stimulus wavelength is performed by providing light from a laser through a stimulus light fiber of the falloposcope.

4. The method of claim 1 wherein emitting light of the first stimulus wavelength is performed by energizing a light emitting semiconductor device located in the falloposcope tip.

5. The method of claim 1, further comprising inserting a guide wire through the lumen to a determined position, and inserting the falloposcope over the guide wire.

6. The method of claim 1, wherein positioning the falloposcope tip near an object comprises inserting the falloposcope through lumens of vagina, cervix, uterus, and fallopian tube of a patient such that the falloposcope tip is in proximity to a first fallopian tube or ovary of the patient, wherein the observed object is the first fallopian tube or ovary of the patient, and wherein the suspect abnormalities are tissue of the fallopian tube or ovary having characteristics consistent with cancerous tissue.

7. The method of claim 1, further comprising using a steering wire controlled by a knob on a steering handle to help position the falloposcope tip.

8. The method of claim 1, further comprising inserting a guide wire through a lumen to a determined position, and inserting the falloposcope over the guide wire.

9. The method of claim 1 further comprising:
    emitting light of a second fluorescence stimulus wavelength from the tip of the falloposcope while imaging light at a second fluorescence emission wavelength, to form at least one second fluorescence emissions image of the object;

imaging the object at the second fluorescence stimulus wavelength to form a second stimulus wavelength image.

10. The method of claim 9, wherein the step of inserting a falloposcope through a lumen is performed by observing the falloposcope and a portion of lumen with a hysteroscope.

11. The method of claim 10, further comprising inflating a lateral everting balloon to aid positioning the OCT channel by pressing the falloposcope against the suspect abnormalities, and where the OCT channel is side viewing from a side of the falloposcope opposite the lateral everting balloon.

12. The method of claim 11, further comprising using a steering wire controlled by a knob on a steering handle to help position the falloposcope tip.

13. The method of claim 9 wherein the step of determining suspect abnormalities of the object is performed on an image processor adapted to control an illuminator configured to perform the step of emitting light at the first fluorescence stimulus wavelength and to perform the step of emitting light of the second stimulus wavelength and generate enhanced images from images received by the image processor from an image sensor configured to perform the steps of imaging light at the first fluorescence emission wavelength and the step of imaging the object at the second fluorescence stimulus wavelength; the image processor configured to prepare enhanced images from images captured by the image sensor.

14. The method of claim 13, further comprising inflating an everting balloon to aid positioning the OCT channel adjacent the object.

15. The method of claim 14, wherein positioning the falloposcope tip near an object comprises inserting the falloposcope through lumens of vagina, cervix, uterus, and fallopian tube such that a tip of the falloposcope is in proximity to a first fallopian tube or ovary of the patient, wherein the object is the first fallopian tube or ovary of the patient, and the abnormality is tissue of the fallopian tube or ovary having characteristics consistent with cancerous tissue.

16. The method of claim 13 wherein the enhanced images include images generated from ratios of reflected light at the first and second stimulus wavelengths and fluorescence emissions obtained during illumination at the first and second stimulus wavelengths.

17. The method of claim 9 further comprising generating ratios of images at the first fluorescence stimulus wavelength and the first fluorescence emissions wavelength, and ratios of images at the second fluorescence stimulus wavelength and the second fluorescence emissions wavelength.

* * * * *